United States Patent
Jenkins et al.

(10) Patent No.: US 12,419,941 B2
(45) Date of Patent: Sep. 23, 2025

(54) POULTRY DRINKING WATER-BASED VACCINE DELIVERY SYSTEM AND METHOD

(71) Applicants: The United States of America, as Represented by the Secretary of Agriculture, Washington, DC (US); Zoetis Services LLC, Parsippany, NJ (US)

(72) Inventors: Mark C Jenkins, Davidsonville, MD (US); Jonathan L Schaeffer, Raleigh, NC (US)

(73) Assignees: The United States of America, as represented by the Secretary of Agriculture, Washington, DC (US); ZOETIS SERVICES LLC, Parsippany, NJ (US)

( * ) Notice: Subject to any disclaimer, the term of this patent is extended or adjusted under 35 U.S.C. 154(b) by 248 days.

(21) Appl. No.: 17/868,571

(22) Filed: Jul. 19, 2022

(65) Prior Publication Data

US 2024/0024447 A1    Jan. 25, 2024

(51) Int. Cl.
*A61K 39/012* (2006.01)
*A61K 39/00* (2006.01)
*A61P 33/02* (2006.01)

(52) U.S. Cl.
CPC ............ *A61K 39/012* (2013.01); *A61P 33/02* (2018.01); *A61K 2039/52* (2013.01); *A61K 2039/552* (2013.01)

(58) Field of Classification Search
None
See application file for complete search history.

(56) References Cited

U.S. PATENT DOCUMENTS

2013/0017220 A1* 1/2013 Jenkins ................ A61K 9/0056
424/269.1

OTHER PUBLICATIONS

Vermeulen et al. Advanced Drug Delivery vol. 54, pp. 795-798-3, 2002 (Year: 2002).*
Ganapathy et al. Vaccine, vol. 28, pp. 3944-3948, 2010. (Year: 2010).*

* cited by examiner

*Primary Examiner* — Jana A Hines
*Assistant Examiner* — Khatol S Shahnan Shah
(74) *Attorney, Agent, or Firm* — John Fado; Matthew Busan (57) ABSTRACT

The drinking water-based avian coccidiosis vaccine formulation and delivery system is structured to deliver a vaccine containing live *Eimeria* oocysts to poultry house brood chamber chicks. The vaccine is delivered to the chicks in a diluted form through the poultry house drinking water system. The chicks are inoculated with the drinking water-based avian coccidiosis vaccine when they consume the water containing the vaccine. The timing of the chicks' drinking water access to the diluted drinking water vaccine is critical. During the inoculation process, water is temporarily withheld from the chicks for a waiting period of about 3-5 hours, and access to the diluted drinking water-based vaccine is limited to an accessibility period of about 2 hours. Additionally, metering valves and/or terminal metering valve assemblies are manually or automatically closed when the when the drinking water lines are fully charged with the diluted vaccine.

11 Claims, 4 Drawing Sheets

POULTRY DRINKING WATER-BASED VACCINE DELIVERY SYSTEM AND METHOD

FIELD OF THE INVENTION

The disclosed subject matter relates to a drinking water-based vaccine for poultry house chicks. Specifically, the subject matter described herein relates to a system and method for formulating a drinking water-based avian coccidiosis vaccine. The vaccine is delivered to poultry house brood chamber chicks in a diluted form through the poultry house drinking water system. The chicks are inoculated with the avian coccidiosis vaccine when they consume the diluted vaccine in the form of drinking water.

BACKGROUND OF THE INVENTION

Avian coccidiosis is an intestinal parasitic disease of poultry caused by protozoa in the genus *Eimeria* that inflicts over $15 billion in annual losses to the worldwide poultry industry. *Eimeria maxima* is the most important coccidian affecting broiler chicken health because it invades and develops in a region of the gut that is important to nutrient absorption (jejunum-ileum). Moreover, *E. maxima* is the predominant *Eimeria* predisposing chickens to the devastating disease necrotic enteritis (NE) caused by *Clostridium perfringens* that exist in high numbers in poultry litter.

For decades the disease has been controlled by medicating poultry feed with ionophore drugs or synthetic chemicals that prevent development of *Eimeria*. However, the emergence of drug-resistant *Eimeria* strains and consumer demand for chickens raised without antibiotics has led to increased use of coccidiosis vaccines. One current non-antibiotic coccidiosis vaccine is based on a "spray" application of a low dose mixture of *Eimeria* oocysts. In theory, chicks sprayed with the coccidiosis vaccine become immunized against coccidiosis by ingesting the vaccine while the chicks are in a shipping box as the chicks are moved from their hatchery to a poultry house brooding area.

For the purposes of this disclosure, a "coccidiosis spray vaccine" is defined as an *Eimeria* oocyst vaccine delivered to chicks in the form of a spray while the chicks are in a shipping box as the chicks are moved from their hatchery to a poultry house brooding area. The coccidiosis spray vaccine is delivered to the chicks when the chicks are about a day old or less.

The use of a low dose *Eimeria* oocyst vaccine mixture is based on the well-established protective immunity that develops in poultry after a primary *Eimeria* infection. However, the inventors' research shows that the currently available spray vaccination is neither uniform nor efficient—with as few as 30% of newly hatched chicks ingesting a sufficient amount of the vaccine to develop immunity to coccidiosis. This current level of effectiveness is generally unsatisfactory for commercial operations.

Although there have been some attempts at delivering various vaccines to poultry through poultry house drinking water systems, past attempts have been unsuccessful or inconsistent. However, the inventors have surprisingly and unexpectedly found that the success of the delivery of some liquid drinking water-based vaccines (including an *Eimeria* oocyst vaccine) via poultry house waterlines is dependent upon the relatively rapid delivery of the vaccines.

The inventors found that time is of the essence in the successful delivery of the vaccine. Among other factors, prior attempts to use drinking water-based vaccines failed because the attempts were directed to hatchery age chicks (about a day old or less) that had not developed the desire to consume a sufficient amount of the liquid vaccine to become inoculated. Prior attempts also failed because the vaccine was allowed to remain in the drinking water lines for more than 2 hours so that the *Eimeria* oocysts were allowed to "settle out" in the poultry house waterlines, and because the chicks were not motivated to consume a sufficient amount of the vaccine when the vaccine was made available to the chicks.

The need exists for an improved commercial-scale avian coccidiosis vaccine delivery system and protocol that is more effective than the current coccidiosis spray vaccine. The system described herein comprises a drinking water-based vaccine formulation and delivery system that supplies the vaccine to the chicks in a timely manner. The current vaccine system and protocol also address the reasons why prior attempts to use drinking water-based vaccines failed. The system and method described herein has a greater than about 90% (mean) success rate. The inventors' proposed system can be automated, requires only one or two trained technicians to operate, and requires minimal modifications to most common poultry house drinking water systems.

SUMMARY OF THE INVENTION

This disclosure is directed to a system and method for inoculating poultry chicks with a diluted drinking water-based avian coccidiosis vaccine (i.e. the diluted drinking water-based vaccine) 28.

Figure 1:
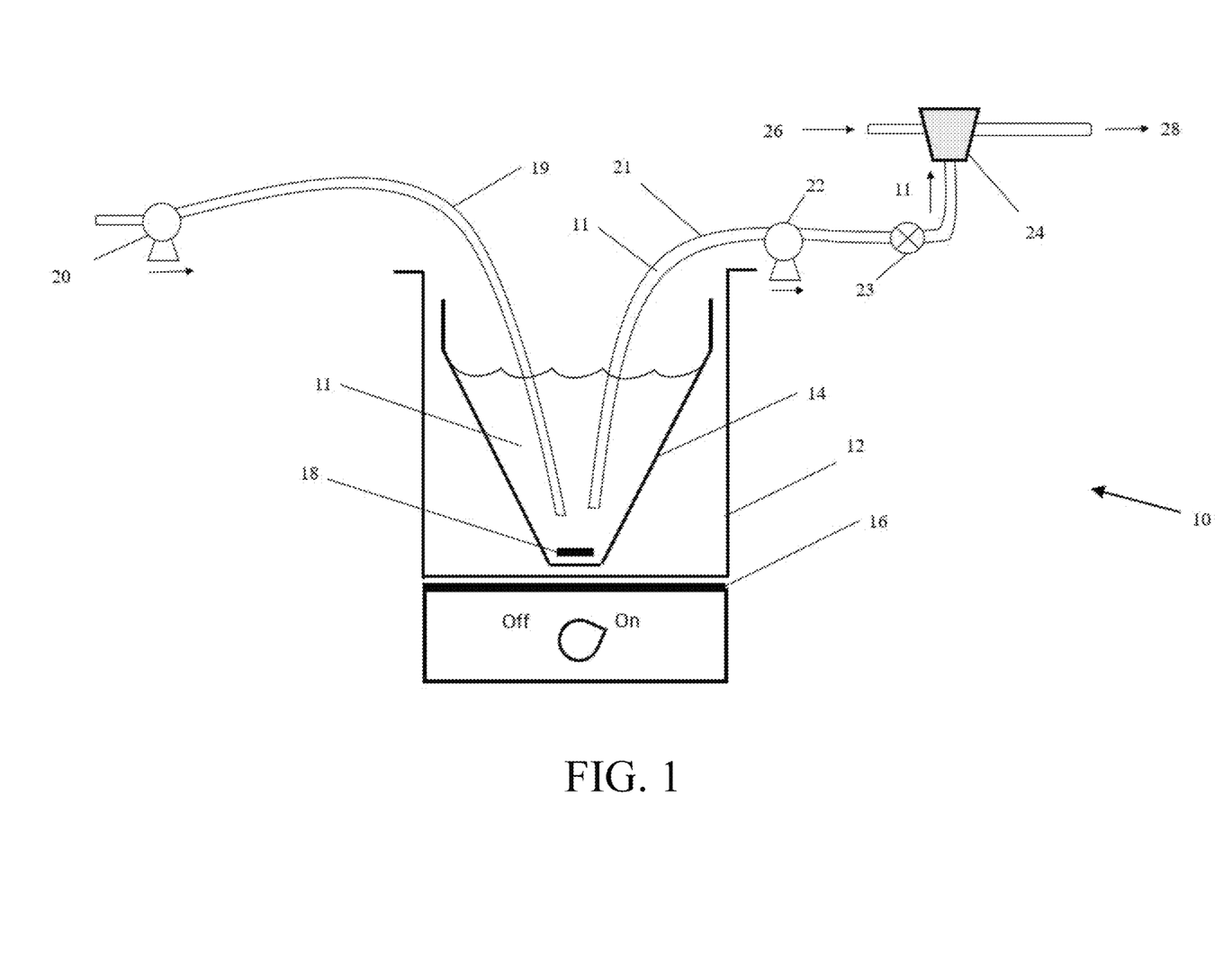
FIG. 1 is a schematic showing a preferred embodiment of the drinking water-based vaccine mixing system 10.

As shown in FIG. 1, a stock solution of live *Eimeria* oocysts and drinking water are mixed to formulate the drinking water-based vaccine 11. A selected color dye may also be added to the vaccine. The drinking water-based vaccine 11 is directed to a medicator 24 and further blended with poultry house drinking water 26 to formulate the diluted drinking water vaccine 28.

Figure 2:
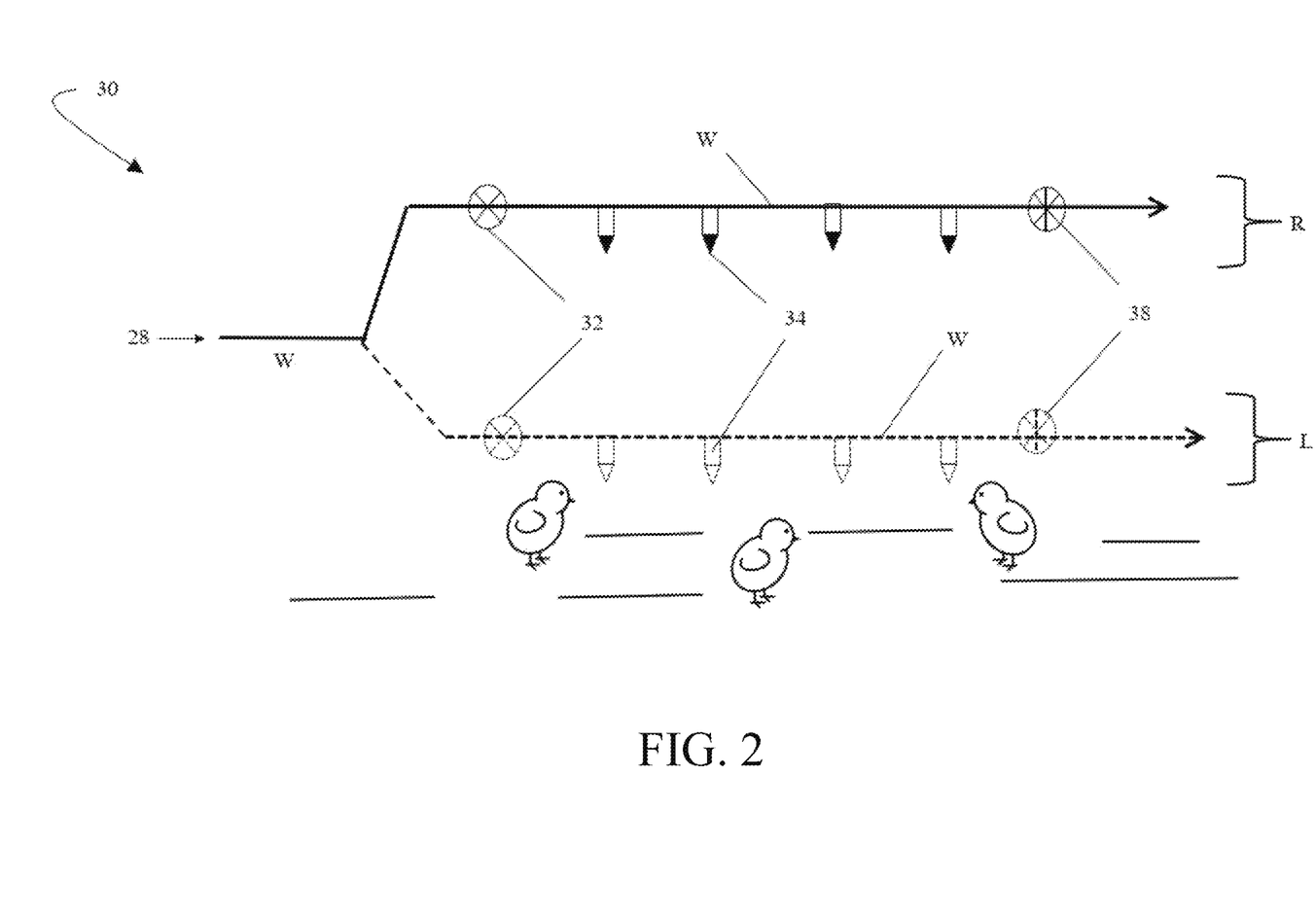
FIG. 2 is a schematic of a basic diluted drinking water-based vaccine delivery system 30. The solid line drawing of the waterlines W in the upper part of FIG. 2 shows the poultry house waterlines W in their initial raised position R. The dashed/ghosted lines in the lower part of FIG. 2 show the poultry house waterlines W in their lowered position L so that the waterlines W (and the diluted drinking water-based vaccine) are accessible to the chicks.

As shown in FIG. 2, after a waiting period in which hydration is withheld from chicks in a poultry house brooding area, poultry house waterlines W that are in a raised position R are charged with the diluted drinking water-based vaccine 28, and then the waterlines W are moved to a lowered position L so that the diluted drinking water-based vaccine 28 in the waterlines W is accessible to the chicks for an accessibility period, wherein during the accessibility period, the chicks in the brooding area consume the diluted drinking water-based vaccine 28 and are inoculated.

Note that assemblies/systems in some of the FIGs. may contain multiple examples of essentially the same component. For simplicity and clarity, in some FIGs., only one (or a few) of the example components may be identified with a reference number. Unless otherwise specified, other non-referenced components with essentially the same structure as the exemplary component should be considered to be identified by the same reference number as the exemplary component. Also note that the images shown in the FIGs. are not intended to be precisely to scale.

DETAILED DESCRIPTION OF PREFERRED EMBODIMENTS

This disclosure is directed to a system 10 for formulating a drinking water-based avian coccidiosis vaccine 11. As shown in FIG. 1, the vaccine 11 is formulated in a conical reservoir 14. The vaccine 11 is pumped 22 from the reservoir 14 through a metering valve 23 to a medicator 24 where the vaccine is blended/diluted with drinking water 26 to formulate a diluted drinking water vaccine 28. As shown in FIG. 2, after a waiting period, the diluted drinking water vaccine 28 flows to the chicks in a poultry house brooding area through poultry house drinking waterlines W. The diluted vaccine 28 flows through the poultry house drinking waterlines to a system of drinking water nipples 34 installed on the drinking water lines W that are selectively made available to the chicks during an accessibility period. The chicks are inoculated with the vaccine when they consume the diluted drinking water vaccine 28 from the nipples 34 within the accessibility period. In the preferred embodiment, the accessibility period is a minimum of 1 hour and a maximum of 2 hours.

Definitions

For the purposes of this disclosure, "avian coccidiosis drinking water-based vaccine" 11 is defined as a liquid coccidiosis vaccine comprising a concentrated stock solution containing live *Eimeria* oocysts that is mixed with drinking water. The vaccine may also contain a selected color dye. In this disclosure, the terms "drinking water-based vaccine", "drinking water vaccine", "water vaccine" and "vaccine" are used interchangeably to describe the drinking water-based avian coccidiosis vaccine 11.

The term "diluted avian coccidiosis drinking water-based vaccine" 28 is defined as comprising a drinking water vaccine 11 that is blended with (and diluted by) additional drinking water 26 as the vaccine 11 flows through the medicator 24, as shown in FIG. 1. Typically, the medicator 24 blends about 1 ounce of vaccine 11 into each gallon of drinking water to formulate the liquid diluted drinking water-based vaccine 28, although the exact mix ratio may vary depending upon the specific equipment, vaccine, and environment associated with a specific application. In this disclosure, the terms "diluted drinking water-based vaccine" "diluted drinking water vaccine", "diluted water vaccine" and "diluted vaccine" are used interchangeably to describe the diluted drinking water-based avian coccidiosis vaccine. The diluted vaccine may also be described as "the drinking water-based vaccine in a diluted form".

The term "drinking water" is defined as any water-based liquid that can be safely consumed by poultry.

The term "medicator" 24 is defined as a blending pump that blends additional poultry house drinking water 26 with the vaccine 11 to formulate the diluted vaccine 28, as shown in FIG. 1. As noted supra, the medicator 24 typically blends about 1 ounce of vaccine 11 into each gallon of drinking water to formulate the diluted vaccine 28.

The "poultry house waterline(s)" W are defined as the piping and valves present between the medicator 24 and the end of the waterlines W that supply drinking water to the poultry house brooding area chicks. The terms "poultry house waterlines" W, "poultry house drinking waterlines", "drinking waterlines" and "waterlines" are used interchangeably.

The term "charged poultry house waterlines" refers to poultry house waterlines W that are "charged" i.e. filled with the diluted vaccine when the waterlines W are in the raised position R as shown in FIG. 2. The waterlines W are promptly charged with the diluted vaccine after the end of the waiting period and before the beginning of the accessibility period. In alternative embodiments, the waterlines W may be charged after the waterlines W are moved to the lowered position L and during the accessibility period.

The "drinking nipples" are the nipples 34 that are installed near the end portions of the poultry house waterlines W. The chicks access and consume the diluted vaccine 28 through the drinking nipples 34.

"Metering valves" 32 are valves that track the amount of the vaccine or diluted vaccine that passes through the metering valves. The metering valves 32 may be selectively opened, closed, monitored, or programmed to operate automatically by operational personnel, as required. The metering valves may be closed manually or they may be battery-operated and comprise an automatic cutoff switch.

"Terminal metering valve assemblies" 38 comprise metering valves and associated assemblies that include at least one transparent component and/or at least one component configured to sense a selected color dye's presence in the diluted drinking water-based vaccine 28. Terminal metering valves 38 may be configured to be closed manually or automatically by operational personnel when the selected colored dye in the diluted drinking water-based vaccine 28 passes and through the terminal metering valve assembly and is visually identified or electronically/optically sensed. Terminal metering valve assemblies 38 may be selectively opened, closed, or programmed to operate automatically by operational personnel, as required. In one preferred embodiment, terminal metering valve assemblies 38 are battery operated and comprise an optical sensor connected to a solenoid valve which automatically closes the valve when the selected color dye is sensed.

The term "waiting period" is defined as a period wherein water is withheld from the chicks so that at the conclusion of the waiting period, the chicks are motivated to consume the diluted vaccine. In the preferred embodiment, the waiting period is about 4 hours. However, in alternative embodiments, the waiting period may vary from 3 to 5 hours depending upon the equipment, vaccine, and environment associated with a specific application. The inventors found that the waiting period does not substantially harm the chicks, but at the end of the waiting period the chicks are motivated to consume a sufficient amount of the diluted vaccine to be inoculated. The "accessibility period" preferably begins when the waiting period ends.

The term "accessibility period" is defined as the period wherein the charged waterlines W (specifically the drinking nipples 34 on the waterlines W) are made available/accessible to the poultry house brood area chicks so that during the accessibility period, the brood area chicks consume a sufficient amount of the diluted vaccine 28 to be inoculated. The accessibility period may be a minimum of one hour to allow the chicks to consume the diluted vaccine, although the chicks may consume the vaccine in less than an hour depending upon the number of chicks, the number of drinking water nipples, the health and vitality of the chicks, etc. However, the accessibility period should not be more than 2 hours because the *Eimeria* oocysts in the poultry house drinking lines W will "settle out" if the diluted vaccine remains in the waterlines for more than about 2 hours. In the preferred embodiment, the accessibility period is about 2 hours.

Technical Problem

The inventors observed that vaccine delivery and accessibility times are of the essence. The diluted drinking water vaccine 28 is preferably delivered to the chicks after the chicks are removed from the hatchery and moved to a brood chamber of a poultry house. Young chicks are typically kept in a brood area after leaving the hatchery and for up to the first two weeks of life. It is critical to expose the chicks to the diluted vaccine 28 before they are infected by the *Eimeria* oocysts that frequently reside in the poultry house litter.

The inventors' research indicates that 3 days after hatching is the optimum time to vaccinate the chicks because there is a substantial increase in water consumption between days 2-3. About two days old was determined to be the minimum age for effective vaccination. Administration of the diluted drinking water vaccine 28 before the chicks are about 2 days old is ineffective because chicks are not consuming sufficient water and are relying mostly on the yolk sac for moisture. Administering the diluted vaccine 28 later than 3 days after hatching gradually increases the risk that the chicks may ingest a significant amount of *Eimeria* oocysts through the poultry house litter—which would affect flock health and predispose chicks to diseases such as necrotic enteritis and gangrenous dermatitis. About 2-4 days of age was determined to be the preferred vaccination age range.

The inventors noted that previous vaccination/inoculation attempts using a water-based vaccine failed or were inconsistent because the *Eimeria* oocysts "settled out" and became trapped in a biofilm inside the poultry house drinking water supply lines W between the medicator 24 and the poultry house drinking water nipples 34. In the preferred embodiment, if the diluted vaccine 28 remains in the drinking water supply lines for longer than an accessibility period of about 2 hours, the inoculation may not be successful.

Additionally, the inventors discovered that the chicks must be motivated to consume a sufficient amount of the diluted vaccine 28 when the diluted vaccine 28 becomes accessible. The inventors observed that, in the normal course of activity, chicks occasionally drank some of the diluted vaccine 28 from the drinking nipples 34, but they did not consume a sufficient amount of the diluted vaccine 28 to become inoculated before the *Eimeria* oocysts in the diluted vaccine 28 "settled out" in the waterlines W. However, the inventors found that, if the diluted vaccine 28 is withheld from the chicks for a "waiting period", at the end of the waiting period, the chicks were motivated to expeditiously consume a sufficient amount of the diluted vaccine 28 to be successfully vaccinated. As described supra, in the preferred embodiment, the waiting period is about 3-5 hours.

Further with regard to the technical problem, the use of basic metering valves 32 and terminal metering valve assemblies 38 may enable operational personnel to determine and/or confirm that poultry house drinking waterlines W are fully charged with the diluted vaccine 28 before the poultry house drinking waterlines are made accessible to the brood house chamber chicks. This process is described in more detail infra.

Detailed System Description

As best shown in FIG. 1, in the preferred embodiment, the water vaccine is preferably mixed in a control room adjoining or near the poultry house. The control room generally contains the drinking water supply equipment for the poultry house. The water vaccine mixing system 10 comprises a conical vaccine formulation reservoir 14 positioned inside a portable mixing container 12.

As shown in FIG. 1, at the beginning of the vaccine mixing process, the reservoir 14 is filled with a combination of drinking water and a concentrated stock solution of live *Eimeria* oocysts. Commercial coccidiosis vaccines are generally supplied in 10,000 dose vials. The number of vials added into the reservoir 14 is based on the number of chicks in the brooder area of the poultry house—with each chick getting a single dose (~300 *Eimeria maxima*/dose).

In the preferred embodiment, a color dye may be mixed into the vaccine 11 while the vaccine is formulated in the vaccine reservoir 14. The purpose of the dye is to enable operational personnel to visually (and/or electronically) identify water containing the diluted vaccine 28 from any common drinking water in the waterlines W. This aspect of the invention will be discussed in greater detail infra.

The volume of the vaccine 11 used in the reservoir 14 is calculated based on: a) the medicator 24 delivering about 1 ounce of the vaccine to every gallon of drinking water (1:128), b) the number of linear feet of the poultry house water lines W running from the medicator 24 to the end of the end of the poultry house water line W; and, c) the internal diameter of the poultry house water line W.

As shown in FIG. 1, the mixing container 12 sits on (or is attached to) a magnetic stir plate 16 that causes the rapid rotation of a stir bar 18 at the bottom of the conical reservoir 14. The purpose of the stir bar 18 is to ensure adequate mixing of the concentrated *Eimeria* oocysts into the drinking water vaccine 11.

As further shown in FIG. 1, an air injection system further ensures that the live *Eimeria* oocysts are thoroughly mixed into the drinking water vaccine 11. Specifically, an air hose 19 extends to the bottom of the conical reservoir 14. An air pump 20 connected to the air hose 19 provides a continuous stream of air that is injected into the bottom of the reservoir 14. The injected air (in combination with the rotating stir bar 18) preferably create at least partially turbulent conditions in the reservoir 14, and thereby further ensure that the *Eimeria* oocysts are thoroughly mixed into the drinking water in the reservoir 14 to formulate the drinking water vaccine 11.

In the preferred embodiment, the air pump 20 comprises a basic electrical "aquarium-style" air bubbling pump that is non-submersible and is positioned outside the aquarium and continuously injects a stream of air bubbles into the bottom of the drinking water reservoir 14 via the air hose tubing 19. Other types of air injection pumps should be considered within the scope of the invention—consistent with the function of creating at least partially turbulent conditions in the reservoir 14 and thoroughly mixing the *Eimeria* oocysts into the drinking water.

Although, in the preferred embodiment, a magnetic stir bar 18 and an air pump 20 are used to mix the drinking water vaccine 11, other means of mechanically/electronically mixing the vaccine should be considered within the scope of the invention. For example, any magnetic or non-magnetic stirring apparatus may be used. Further, any stirring/blending/shaking/mixing/swirling or otherwise agitating system or apparatus designed to mix the contents of a reservoir—may be used to mix the vaccine 11, including various motion, blades, baffles, paddles, or inertial devices. However, the mixing means is limited by the requirement that the live *Eimeria* oocysts cannot be macerated or otherwise killed in the mixing process.

As the *Eimeria* oocysts and drinking water are mixed to formulate the drinking water vaccine 11, a vaccine transfer pump 22 simultaneously pumps the water vaccine 11 out of the reservoir 14, preferably through plastic water tubing 21. In the preferred embodiment, the vaccine transfer pump 22 comprises an electric water pump. In alternative embodiments, other types of water pumps should be considered within the scope of the invention—consistent with the function of transferring the vaccine.

The vaccine transfer pump 22 pumps the vaccine 11 through a metering valve 23 to a medicator 24. Medicators 24 are relatively common in the poultry industry and are typically used to sanitize water lines, to acidify drinking water, and to introduce medications into the drinking water. As noted supra, medicators 24 are generally set to deliver about 1 oz of stock solution (in this case, drinking water vaccine 11) per gallon of drinking water. However, the mixing/blending rate is selectively adjustable by an operator and may vary based on multiple considerations specific to a specific application.

As shown in FIG. 1, the medicator 24 receives the vaccine 11 from the vaccine transfer pump 22, and also receives poultry house drinking water (shown in FIG. 1 as the arrow 26) from the control room water supply system. The medicator 24 blends the poultry house drinking water 26 with the drinking water vaccine 11. The blended vaccine/drinking water mixture (i.e. the diluted vaccine 28) is ultimately directed to the poultry house brood area waterlines W.

As shown in FIG. 2, the diluted vaccine 28 is pumped from the medicator 24 through the poultry house waterline W into the brood chamber area of the poultry house. Specifically, the diluted vaccine 28 is pumped into a brood chamber waterline(s) W that supplies drinking water to the brood chamber chicks.

Figure 3:
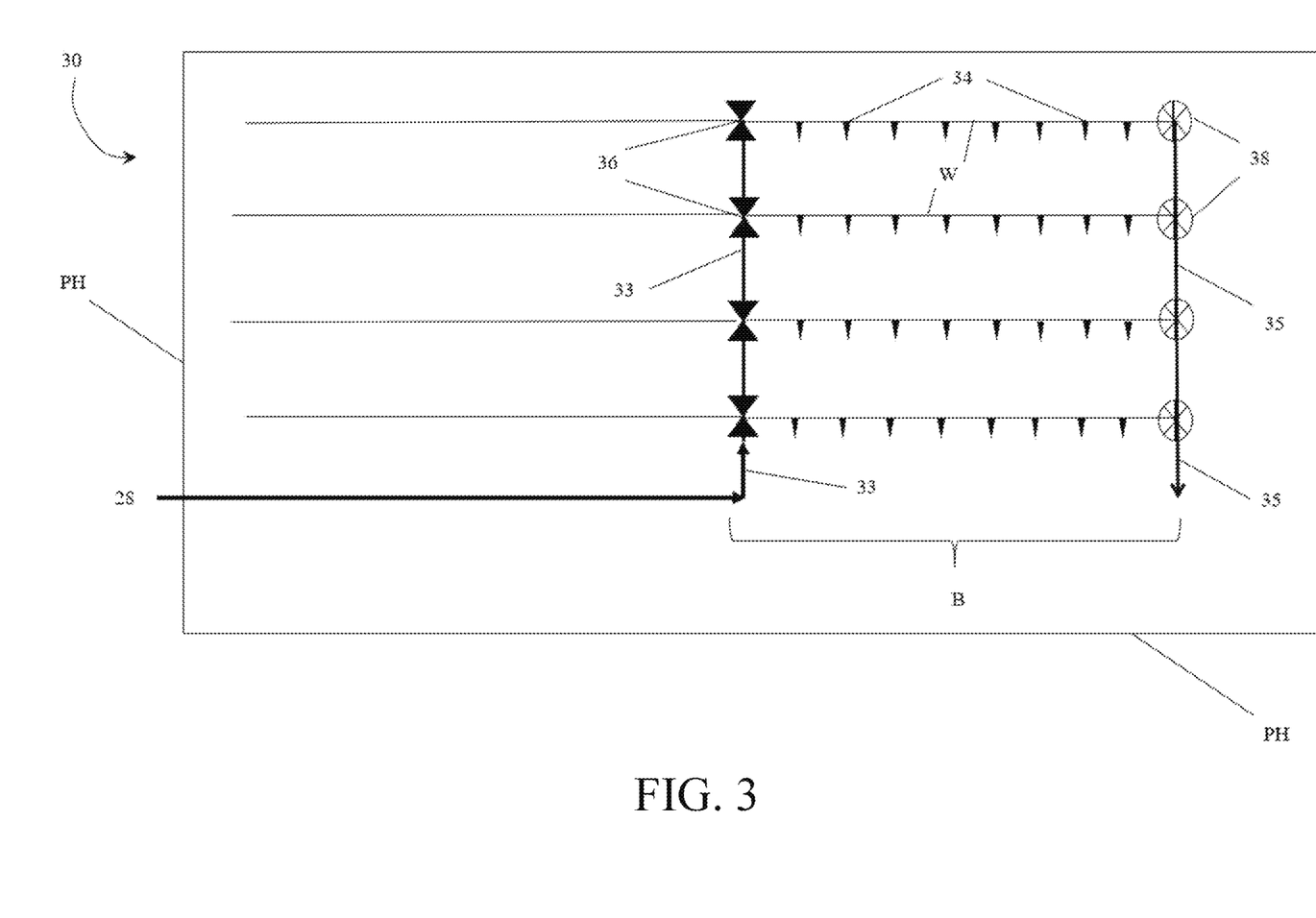
FIG. 3 is a schematic view of a poultry house drinking water system wherein the brooder area is at an end of the poultry house.
Figure 4:
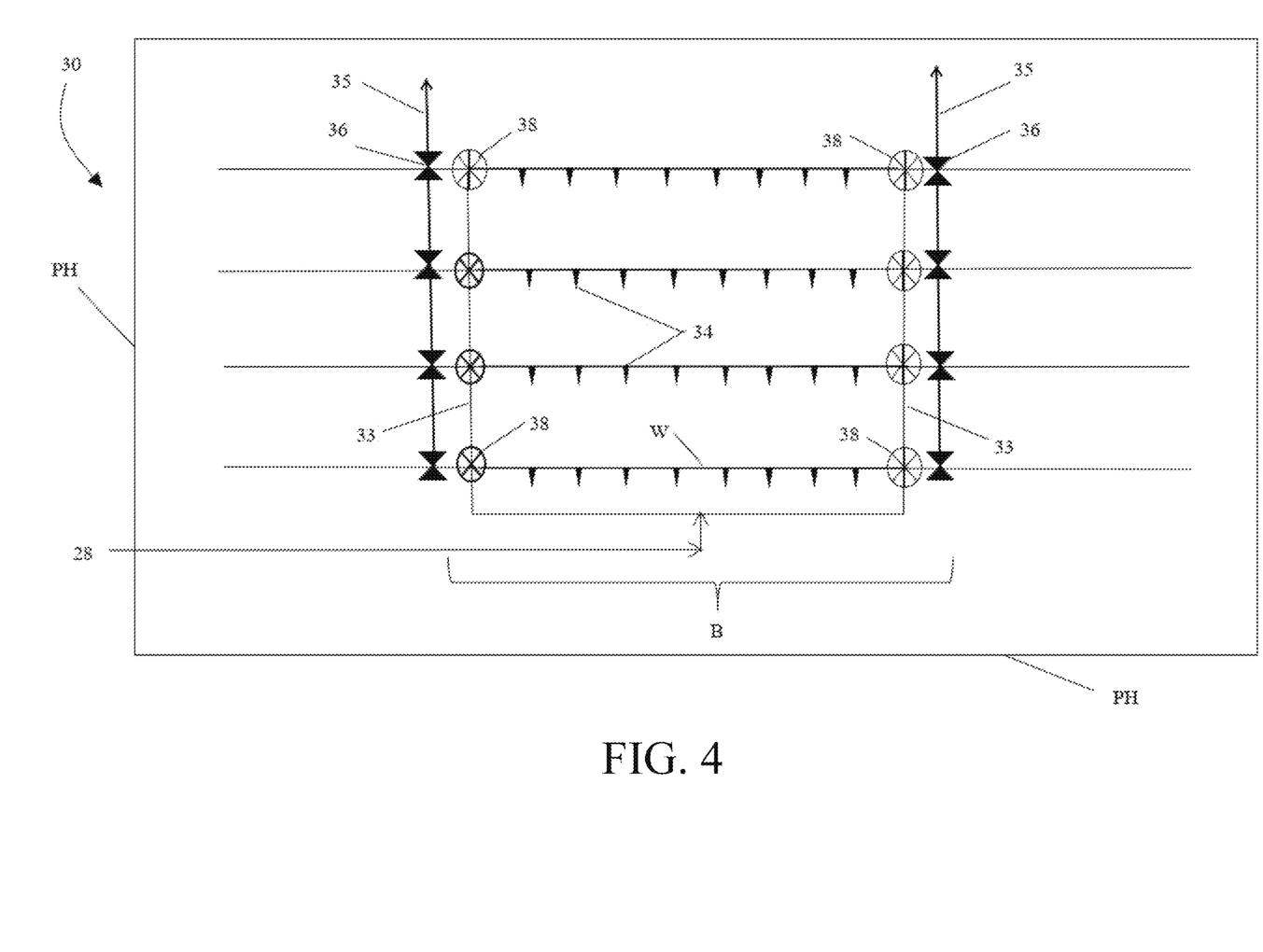
FIG. 4 is a schematic view of a poultry house drinking water system wherein the brooder area is in the center of the poultry house.

Note that FIG. 2 shows a very basic/simplified vaccine delivery system 30 that is included in this disclosure to illustrate and communicate the basic structure and protocols associated with the drinking water vaccine delivery system 30. Although FIG. 2 shows only a single poultry house waterline W and five drinking nipples 34, please note that most commercial poultry operations comprise at least four to six (or more) poultry house waterlines W, with each waterline W having twenty or more water drinking nipples 34. Although the commercial systems are larger, the basic vaccine delivery protocol is essentially the same as the protocol shown and described in FIG. 2. Larger commercial poultry house drinking water delivery systems 30 associated with FIGS. 3 and 4 are discussed infra.

Before beginning the vaccination process, it is critical for any liquid remaining in the pumphouse waterlines W to be removed and replaced with the diluted vaccine 28. The most straight-forward way to accomplish this is simply by calculating the amount of water that must be displaced through the terminal metering valve assembly(s) 38. Once the targeted amount of water flows through the terminal metering valve assembly(s) 38, then the water previously in the lines W has been fully replaced by the diluted vaccine 28 and the drinking water lines W are fully charged with the diluted vaccine 28.

The calculation of the water displacement volume required is based on the formula:

Displacement Volume=(Inside diameter of waterline×0.0408 gal/ft×length of waterline×number of water lines)+(volume of water between pump house and the poultry house waterline junction)

Alternatively or additionally, operational personnel may manually close the terminal metering valve assemblies 38 when the presence of a color dye is visually confirmed at the respective terminal metering valve assemblies 38. As noted supra, terminal metering valve assemblies 38 comprise metering valves and associated assemblies that include at least one transparent component and/or at least one component configured to sense a selected color dye in the diluted drinking water-based vaccine 28. The transparent component may comprise a short section of transparent tubing associated with the opening/closing valve portion of the terminal metering valve assembly 38 that is visible to operational personnel. The operational personnel may rely of the sight of the dye through the transparent component to confirm that the dye has (or has not) reached the terminal metering valve assembly 38.

As a further alternative or additional confirmation, the terminal metering valve assembly 38 may include an electronic indication of the presence of the selected dye at the terminal metering valve assembly 38. Multiple currently available components are capable of performing this task. Typical components include optical imaging receiving devices (such as RGB cameras) that can be programmed to filter light wavelengths other than the wavelengths associated with the color of the dye—and when a filtered image indicates the presence of light wavelengths associated with the of the color of the dye (e.g. pixels), operational personnel are alerted. For example, the company SENSOPART INC. (www.sensopart.com) makes a compact machine vision sensor (model trademark VISOR) that includes target illumination and color detection.

In any case, when the dye is sensed, an electrical signal is promptly sent to a solenoid valve portion of the terminal metering valve assembly 38, and the open/closed valve portion of the terminal metering valve assembly 38 is moved to the closed position. As noted supra, the terminal metering valve assembly 38 may comprise an automatic cutoff switch and be battery-operated.

After the vaccination process is terminated at the end of the accessibility period, the absence of dye-containing solution in the waterlines W is a confirmation that all of the diluted vaccine 28 is exhausted from the waterline W.

As best shown in FIG. 2, the poultry house waterline W comprises a series of drinking nipples 34 that enable the chicks to drink and thereby access the diluted drinking water vaccine 28. In the preferred embodiment, the drinking nipples 34 are spaced about twelve inches apart along the waterline W. The chicks are inoculated when they consume a sufficient amount of the diluted vaccine 28 through the drinking nipples 34.

As shown in FIG. 2, at the beginning of the vaccination process, the poultry house water line W is moved to the raised position R so that hydration (i.e. water/diluted vaccine 28) is withheld from the chicks in the brood chamber area for a waiting period. As noted supra, in the preferred embodiment the waiting period is about four hours, however in alternative embodiments, the waiting period may be from 3-5 hours. The inventors found that the 3-5 hour waiting period does not significantly harm the chicks, and at the end of the waiting period the chicks will consume the maximal/sufficient amount of the vaccine mixture.

In the preferred embodiment, the waterline W is moved to the raised position R via an electrical or hydraulic hoist. In alternative embodiments, the water line can be raised/lowered manually or by any means known in the art. At the end of the waiting period, while the waterlines W are still in the raised position, the waterlines W are fully charged (i.e. filled) with the diluted vaccine 28.

As shown in FIG. 2, at the end of the waiting period and (preferably) after the waterline W is charged, the waterline W is moved to a lowered position L—as shown by the dashed lines in the lower portion of FIG. 2. In the lowered position L, the chicks can easily access the waterline W drinking nipples 34. The inventors found that essentially all of the chicks were able to consume a sufficient amount of the diluted drinking water vaccine 28 for inoculation within about one hour of lowering the drinking water lines and giving the chicks access to the drinking nipples 34. In the preferred embodiment, the drinking lines remain available for about an additional hour so that the total accessibility period is about 2 hours.

As shown in Table 1, the inventors conducted a series of four trials to determine the effectiveness of the drinking water vaccine formulation system and operational protocol. The inventors' data shows that the proposed system and protocol results in a greater than 90% (mean) uptake of the coccidiosis vaccine.

TABLE 1

Uptake of *Eimeria maxima* oocysts in chicks given *E. maxima* oocysts by spray-vaccination at the hatchery (0 day), or through a liquid drinking water vaccine system at 3 days of chick age.

| Treatment | Positive chicks/total (%+) | Mean log number oocysts shed | Median log number oocysts shed |
|---|---|---|---|
| Trial No. 1 | | | |
| *E. maxima* Spray (APU2 + B52) | 10/16 (63%) | 5.5 ± 5.5 | 4.8 |
| *E. maxima* Water Only (APU2 + B52) | 16/16 (100%) | 5.7 ± 5.6 | 5.6 |
| None | 3/16 (19%) | 5.0 ± 5.2 | 0.0 |
| Trial No. 2 | | | |
| *E. maxima* Spray (B52) | 0/16 (0%) | 0.0 | 0.0 |
| *E. maxima* Water Only (B52) House 1 | 13/16 (81%) | 4.4 ± 4.6 | 4.5 |
| *E. maxima* Water Only (B52) House 2 | 14/16 (88%) | 5.0 ± 4.9 | 4.5 |
| Trial No. 3 | | | |
| *E. maxima* Spray (B52) | 0/16 (0%) | 0.0 | 0.0 |
| *E. maxima* Water Only (B52) | 14/16 (88%) | 5.0 ± 5.3 | 4.3 |
| *E. maxima* Water Only (B52 + APU2) | 14/16 (88%) | 5.1 ± 5.0 | 4.8 |
| Trial No. 4 | | | |
| *E. maxima* Spray (B52) | 0/16 (0%) | 0.0 | 0.0 |
| *E. maxima* Water Only (B52) | 15/16 (94%) | 5.0 ± 5.0 | 5.6 |
| Compilation of all *E. maxima* oocysts output arising from different methods of delivering vaccine (Trials 1-4) | | | |
| *E. maxima* Spray Only (n = 4) | Mean = 16% ± 27% | | Median = 0% |
| *E. maxima* Water Only (n = 6) | Mean = 90% ± 6% | | Median = 85% |

Protocol Description

In operation, poultry operations personnel mix/formulate the drinking water vaccine 11 using the water vaccine formulation system 10 shown in FIG. 1. Specifically, poultry operations personnel add a concentrated live *Eimeria* oocysts stock solution, drinking water, and a selected color dye to a conical drinking water reservoir 14. The drinking water, *Eimeria* oocysts, and selected color dye are mixed using at least a stirring/blending means. In the preferred embodiment, the stirring/blending means comprises a magnetic stir bar 18, and an air pump 20 that injects water bubbles into the reservoir 14.

As further shown in FIG. 1, as the drinking water vaccine 11 is mixed, the mixed/formulated vaccine is pumped out of the reservoir 14 by a vaccine transfer pump 22, through a metering valve 23 to a medicator 24. The medicator 24 comprises a blending pump which further blends the drinking water vaccine 11 with poultry house drinking water 26 to create a diluted drinking water vaccine 28.

In the preferred embodiment, during about a 3-5 hour waiting period, poultry house chicks in the brood area of the poultry house are deprived of water. After the end of a waiting period, the diluted vaccine 28 flows into the poultry house waterlines W from the medicator 24 and charges the poultry house waterlines W, as best shown in FIG. 2. The poultry house waterlines W are charged while the waterlines W are in the raised position R. The diluted vaccine 28 completely replaces any liquid present in the poultry house waterlines W. Operational personnel may use terminal metering valve assemblies 38 to confirm that the poultry house waterlines W are fully charged.

After the waiting period is over and the poultry house waterlines W are charged, the poultry house waterlines W are moved to a lowered position so that the chicks have access to the drinking nipples 34 for an accessibility period. In the preferred embodiment, the accessibility period is about two hours long. By the end of the accessibility period, the chicks become satiated and typically consume a sufficient amount of the diluted vaccine 28 for inoculation.

The inventors' data shows that the drinking water vaccine formulation and delivery system 10, 30, and the associated operational protocol described herein results in a greater than mean 90% (mean) uptake of the avian coccidiosis vaccine.

EXAMPLES

As noted supra, most commercial poultry production operations occur on a large scale (18,000-42,000 chicks/house). As shown in FIGS. 3 and 4, in the U.S. and worldwide, poultry houses PH are typically about 500-650 feet long and about 40-60 feet wide. The poultry houses PH have a brood chamber area B that comprises about 40% of the poultry house PH. Young chicks are usually kept in the brood chamber area B after leaving the hatchery for the first 7-10 days of life. These brood chambers are typically either located at one end (per FIG. 3) or in the center (per FIG. 4) of the poultry house PH. Each poultry house PH frequently includes a network of valves and a variety of other liquid flow control hardware. Each waterline W also includes a plurality of drinking water nipples 34. As noted supra, in most commercial poultry operations, each waterline W should have one nipple drinker/foot of water line providing one drinker 34 for every 10-15 chicks. Note that, for the sake of simplicity, not all of the hardware necessary to control the flow of drinking water is shown in FIGS. 3-4.

In the FIG. 3 embodiment, the diluted vaccine 28 flows up a water distribution line 33 in the center of the poultry house PH—which coincides with the left side of the poultry house brood area B. Access to each of the poultry house waterlines W is controlled by an inline ball valve 36. Preferably, the diluted vaccine 28 flows through the ball valves 36 and into the respective waterlines W—pushing whatever liquid was present in the waterlines W out through the water metering valves 32 (specifically terminal metering valve assemblies 38) in the current disclosure and down a drain line 35.

In the FIG. 4 embodiment, the diluted vaccine 28 flows into the poultry house PH and is then split into two vaccine distribution lines 33. Each of the two vaccine distribution lines 33 flows around opposite outside edges of the brooding area B—which is located in the center of the poultry house PH. Multiple fluid paths are possible for displacing the fluid in the waterlines W and directing the displaced fluid out one or both of the drain lines 35.

For the foregoing reasons, it is clear that the subject matter described herein provides an innovative drinking water vaccine formulation and delivery system that may be used in multiple poultry and other livestock applications. The current system may be modified in multiple ways and applied in various technological applications. The disclosed method and apparatus may be modified and customized as required by a specific operation or application, and the individual components may be modified and defined, as required, to achieve the desired result.

Although most of the materials of construction are not described, they may include a variety of compositions consistent with the function described herein. Such variations are not to be regarded as a departure from the spirit and scope of this disclosure, and all such modifications as would be obvious to one skilled in the art are intended to be included within the scope of the following claims.

The amounts, percentages and ranges disclosed in this specification are not meant to be limiting, and increments between the recited amounts, percentages and ranges are specifically envisioned as part of the invention. All ranges and parameters disclosed herein are understood to encompass any and all sub-ranges subsumed therein, and every number between the endpoints. For example, a stated range of "1 to 10" should be considered to include any and all sub-ranges between (and inclusive of) the minimum value of 1 and the maximum value of 10 including all integer values and decimal values; that is, all sub-ranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions, and so forth as used in the specification and claims are to be understood as being modified in all instances by the implied term "about." If the (stated or implied) term "about" precedes a numerically quantifiable measurement, that measurement is assumed to vary by as much as 10%. Essentially, as used herein, the term "about" refers to a quantity, level, value, or amount that varies by as much 10% to a reference quantity, level, value, or amount. Accordingly, unless otherwise indicated, the numerical properties set forth in the following specification and claims are approximations that may vary depending on the desired properties sought to be obtained in embodiments of the present invention.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to a quantity, level, value, or amount that varies by as much as 10% to a reference quantity, level, value, or amount.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein). The invention illustratively disclosed herein suitably may be practiced in the absence of any element which is not specifically disclosed herein. The term "an effective amount" as applied to a component or a function excludes trace amounts of the component, or the presence of a component or a function in a form or a way that one of ordinary skill would consider not to have a material effect on an associated product or process.

What is claimed is:

1. A system for formulating and delivering a diluted drinking water-based avian coccidiosis vaccine to chicks so that the chicks are inoculated with the diluted drinking water-based vaccine, the system comprising:

a concentrated stock solution of live *Eimeria* oocysts;

a mixing reservoir comprising a mixing means, the mixing means mixing the stock solution of live *Eimeria* oocysts, drinking water, and a selected color dye in the mixing reservoir to formulate a drinking water-based vaccine;

a medicator structured to receive the drinking water-based vaccine and blend additional drinking water into the vaccine to create a diluted drinking water-based vaccine; and, at least one poultry house waterline configured to receive the diluted drinking water-based vaccine from the medicator, the at least one poultry house waterline being in a raised position so that the at least one poultry house waterline is inaccessible to the chicks;

wherein the system is structured so that, at the end of a waiting period, the at least one poultry house waterline is promptly charged with the diluted drinking water-based vaccine and moved to a lowered position so that the chicks have access to the at least one poultry house waterline and the chicks expeditiously consume the diluted drinking water-based vaccine from the at least one poultry house waterline and are inoculated by the diluted drinking water-based vaccine.

2. The system of claim 1 wherein the chicks are inoculated with the diluted drinking water-based vaccine in a brooding area of a poultry house, the chicks being about 2-4 days old.

3. The system of claim 1 wherein the mixing reservoir comprises a conical reservoir and the mixing means comprises a stir bar and an air injection pump, the stir bar and an outlet of the air injection pump being positioned at a bottom of the conical reservoir.

4. The system of claim 1 wherein the diluted drinking water-based vaccine is formulated in the medicator at a ratio of about 1 ounce of vaccine per 1 gallon of drinking water.

5. The system of claim 1 wherein the waiting period is about 3-5 hours.

6. The system of claim 1 wherein, at the end of the waiting period, the at least one poultry house waterline is moved to the lowered position for an accessibility period, the accessibility period being a minimum of about 2 hours.

7. The system of claim 1 wherein the chicks access the diluted drinking water-based vaccine through drinking nipples mounted on the at least one poultry house waterline.

8. The system of claim 1 further comprising at least one terminal metering valve assembly, the at least one terminal metering valve assembly is positioned at an end of each of the at least one poultry house waterlines, the terminal metering valve assembly comprising a means of inspecting the diluted drinking water-based vaccine for the selected color dye at the terminal metering valve assembly, and manually or automatically closing the at least one terminal metering valve assembly when the selected color dye is sensed at the at least one terminal metering valve assembly, thereby ensuring that each of the at least one poultry house waterlines are fully charged with the diluted drinking water-based vaccine.

9. A system for formulating and delivering a diluted drinking water-based avian coccidiosis vaccine to chicks so that the chicks are inoculated with the diluted drinking water-based vaccine, the system comprising:
a concentrated stock solution of live *Eimeria* oocysts;
a conical mixing reservoir comprising a mixing means, the mixing means mixing the stock solution of live *Eimeria* oocysts, drinking water, and a selected color dye in the conical mixing reservoir to formulate a drinking water-based vaccine, wherein the mixing means comprises a stir bar and an air injection pump, wherein the stir bar is configured to undergo rotation via interaction with a magnetic stir plate, and wherein the stir bar and an air hose outlet of the air injection pump are positioned at a bottom of the conical mixing reservoir and configured to create at least partially turbulent conditions in the conical mixing reservoir, thereby ensuring the live *Eimeria* oocysts are thoroughly mixed into the drinking water in the conical mixing reservoir;
a medicator structured to receive the drinking water-based vaccine and blend additional drinking water into the vaccine to create a diluted drinking water-based vaccine; and,
at least one poultry house waterline configured to receive the diluted drinking water-based vaccine from the medicator, the at least one poultry house waterline being in a raised position so that the at least one poultry house waterline is inaccessible to the chicks;
wherein the system is structured so that, at the end of a waiting period, the at least one poultry house waterline is promptly charged with the diluted drinking water-based vaccine and moved to a lowered position so that the chicks have access to the at least one poultry house waterline and the chicks expeditiously consume the diluted drinking water-based vaccine from the at least one poultry house waterline and are inoculated by the diluted drinking water-based vaccine.

10. A system for formulating and delivering a diluted drinking water-based avian coccidiosis vaccine to chicks so that the chicks are inoculated with the diluted drinking water-based vaccine, the system comprising:
a concentrated stock solution of live *Eimeria* oocysts;
a mixing reservoir comprising a mixing means, the mixing means mixing the stock solution of live *Eimeria* oocysts, drinking water, and a selected color dye in the mixing reservoir to formulate a drinking water-based vaccine;
a medicator structured to receive the drinking water-based vaccine and blend additional drinking water into the vaccine to create a diluted drinking water-based vaccine; and,
at least one poultry house waterline configured to receive the diluted drinking water-based vaccine from the medicator, the at least one poultry house waterline being in a raised position so that the at least one poultry house waterline is inaccessible to the chicks;
at least one terminal metering valve assembly, the at least one terminal metering valve assembly is positioned at an end of each of the at least one poultry house waterlines, the terminal metering valve assembly comprising a means of inspecting the diluted drinking water-based vaccine for the selected color dye at the terminal metering valve assembly, and automatically closing the at least one terminal metering valve assembly when the selected color dye is sensed at the at least one terminal metering valve assembly, thereby ensuring that each of the at least one poultry house waterlines are fully charged with the diluted drinking water-based vaccine;
wherein the system is structured so that, at the end of a waiting period, the at least one poultry house waterline is promptly charged with the diluted drinking water-based vaccine and moved to a lowered position so that the chicks have access to the at least one poultry house waterline and the chicks expeditiously consume the diluted drinking water-based vaccine from the at least one poultry house waterline and are inoculated by the diluted drinking water-based vaccine.

11. The system of claim 10 wherein the terminal metering valve assembly comprises an optical sensor so that when the optical sensor senses the selected color dye, the sensor sends an electrical signal to a solenoid component of the terminal metering valve assembly, thereby causing the terminal metering valve assembly to close.

\* \* \* \* \*